United States Patent [19]
Gould

[11] Patent Number: 5,961,537
[45] Date of Patent: Oct. 5, 1999

[54] NOSE FORESHORTENER AND EXTERNAL NASAL DILATOR

[76] Inventor: David L. Gould, 7309 Murdy Cir., Huntington Beach, Calif. 92647

[21] Appl. No.: 08/812,404

[22] Filed: Mar. 5, 1997

Related U.S. Application Data

[60] Provisional application No. 60/012,856, Mar. 5, 1997.

[51] Int. Cl.⁶ .................................................. A61F 5/08
[52] U.S. Cl. ........................................................ 606/204.45
[58] Field of Search ........................... 606/204.45, 199; 128/200.24, 207.18; 602/54, 58, 902, 12, 14, 6, 16, 46–47, 61; 604/304, 307, 308

[56] References Cited

U.S. PATENT DOCUMENTS

| | | | |
|---|---|---|---|
| 5,383,891 | 1/1995 | Walker | 606/199 X |
| 5,476,091 | 12/1995 | Johnson . | |
| 5,533,499 | 7/1996 | Johnson . | |
| 5,533,503 | 7/1996 | Doubek et al. . | |
| 5,538,500 | 7/1996 | Peterson | 606/54 X |
| 5,546,929 | 8/1996 | Muchin . | |
| 5,611,333 | 3/1997 | Johnson | 606/204.45 X |
| 5,611,334 | 3/1997 | Muchin | 606/204.45 |
| 5,653,224 | 8/1997 | Johnson | 606/902 X |
| 5,669,377 | 9/1997 | Fenn . | |
| 5,685,292 | 11/1997 | Fenn | 606/199 X |
| 5,706,800 | 1/1998 | Cronk et al. | 606/199 X |

Primary Examiner—Michael Buiz
Assistant Examiner—Vikki Trinh

[57] ABSTRACT

A removably lined adhesive strip for foreshortening a nose and dilating the nasal passages of the nose. The strip is an external strip with two end portions. One end portion is fixed to a position on or beyond the tip of the nose, such as immediately beyond the tip of the nose and the other end portion is fixed to a position on the bridge of the nose. The strip may be integrally formed with or separate from a spring nasal dilator applied across the bridge of the nose and to the nostril of the nose. The strip may be used with or without such a spring nasal dilator. One preferred embodiment of the strip includes an end portion which is generally the shape of a diamond or arrowhead with rounded tips so as to generally reflect the shape of the tip of the nose or the shape of the nose immediately beyond the tip of the nose. A method for applying the strip includes first applying one end portion to a position on or beyond the tip of the nose and then applying the other end portion to the bridge of the nose.

15 Claims, 10 Drawing Sheets

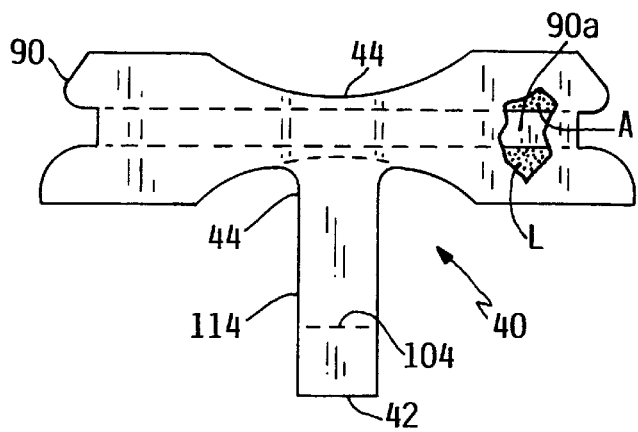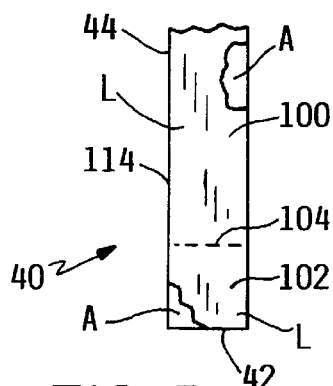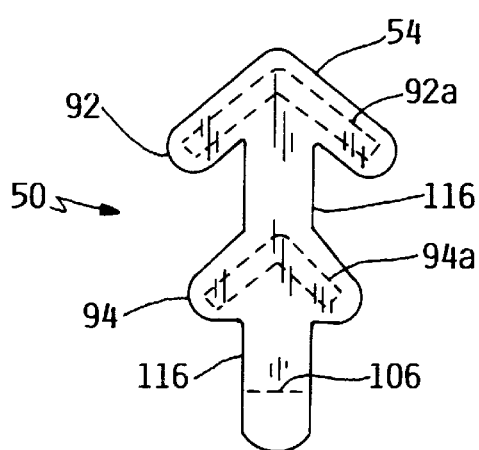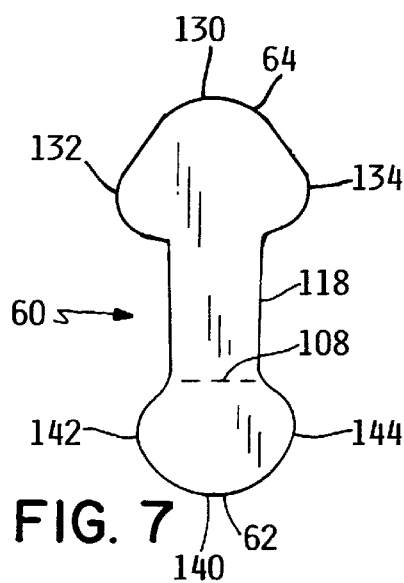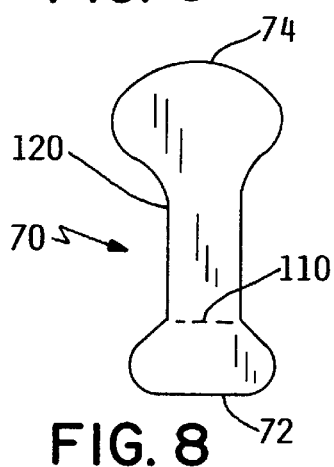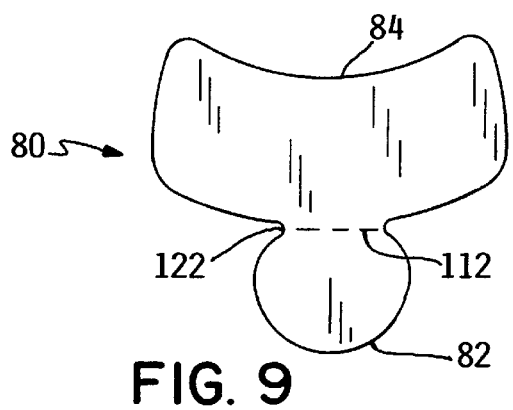

5,961,537

NOSE FORESHORTENER AND EXTERNAL NASAL DILATOR

This application claims the benefit under Title 35, United States Code § 119(e) of the United States provisional application number 60/012,856 filed Mar. 5, 1997 and entitled Nose Foreshortner And External Nasal Dilztor (sic). Such provisional application number 60/012,856 is hereby incorporated by reference in its entirety into this application.

BACKGROUND OF THE INVENTION

The present invention relates generally to strips to be applied to the nose, and specifically to strips for foreshortening the nose.

A spring nasal dilator is a strip of adhesive with a flat spring engaged therein. The spring nasal dilator is applied across the bridge of the nose and has portions which engage the nostrils. When the flat spring is thus bent across the bridge of the nose, it has a bias or tendency to return to its original flat shape and thereby pulls the skin or underlying tissue of the nose outwardly so as to dilate the nasal passages.

SUMMARY OF THE INVENTION

A general object of the present invention is to provide a unique nose foreshortener.

Another object of the invention is to provide for such a nose foreshortener a unique strip with two end portions. Each end portion has an inner adhesive face. One end portion is applied on or beyond the tip of the nose when the tip of the nose is compressed. The other end portion is applied on the bridge of the nose and serves as an anchor to keep the tip of the nose compressed. When the tip of the nose is maintained in such compressed state, the nasal passages are dilated and one may in turn breathe easier and take in more volume. When the tip of the nose is compressed, the alar cartilage, lateral nasal cartilage, cartilage of the nasal septum, and fibro-fatty tissue is compressed so as to dilate the nose. Further when the tip of the nose is so compressed, fibro-fatty tissue and lateral nasal cartilage vibration is minimized, so as to minimize snoring.

Another object of the invention is to provide for such a nose foreshortener a unique shape for one or more of the end portions. A preferred embodiment of the invention includes an end portion shaped generally like a diamond or arrowhead having rounded points. Such a shape generally reflects the shape of the tip of the nose.

Another object of the invention is to provide for such a nose foreshortener a unique liner. The liner includes two liner portions separated by a score. One liner portion has the shape of the end portion to be applied on or beyond the tip of the nose and this liner portion is removed first. The other liner portion is kept on the strip until the tip of the nose has been pushed up or compressed, thereby maintaining the adhesive for the anchor end in a clean non oily state.

Another object of the invention is to provide for such a nose foreshortener a transversely oriented spring nasal dilator. The nose foreshortener may be integral with or formed of a separate piece from the transversely oriented spring nasal dilator.

Another object of the invention is to provide for such a nose foreshortener a strip which may be inverted. In other words, either end portion of the strip may be applied to either the tip of the nose or the bridge of the nose. Each of the end portions may have generally the same shape in such a case.

Another object of the invention is to provide a unique method for applying the nose foreshortener. It is preferred to first apply one end portion on or beyond the tip of the nose and to subsequently apply the anchoring end portion. The anchoring end portion hence is applied only once. Although the steps may be carried out in reverse order, such may result in taking off and reapplying the anchoring end so as to fix the other end portion at a comfortable position on or beyond the end of the nose.

These and further objects and advantages of the present invention will become clearer in light of the following detailed description of the illustrative embodiments of this invention described in connection with the drawings.

BRIEF DESCRIPTION OF THE DRAWINGS

The illustrative embodiments may be best described by reference to the accompanying drawings where:

FIG. 4 shows a top plan view of one embodiment of the present nose foreshortener formed integrally with a spring nasal dilator.

FIG. 5 shows a rear plan view of the nose foreshortener portion of the embodiment of FIG. 4 and illustrates two liner portions and a score between the liner portions.

FIG. 6 shows another embodiment of the invention and illustrates two inverted V-shaped spring nasal dilators.

FIG. 7 shows a top plan view of another embodiment of the present invention having two generally diamond shaped end portions.

FIG. 8 shows a top plan view of another embodiment of the present invention having blunted end portions.

FIG. 9 shows a top plan view of another embodiment of the present invention where one end portion is transversely oriented to extend across the bridge of the nose and where the other end portion, for placement immediately beyond the tip of the nose, is substantially immediately adjacent to the transversely oriented end portion.

All Figures are drawn for ease of explanation of the basic teachings of the present invention only; the extensions of the Figures with respect to number, position, relationship, and dimensions of the parts to form the preferred embodiment will be explained or will be within the skill of the art after the following description has been read and understood. Further, the exact dimensions and dimensional proportions to conform to specific force, weight, strength, and similar requirements will likewise be within the skill of the art after the following description has been read and understood. Where used in the various figures of the drawings, the same numerals designate the same or similar parts.

DESCRIPTION

Figure 13:
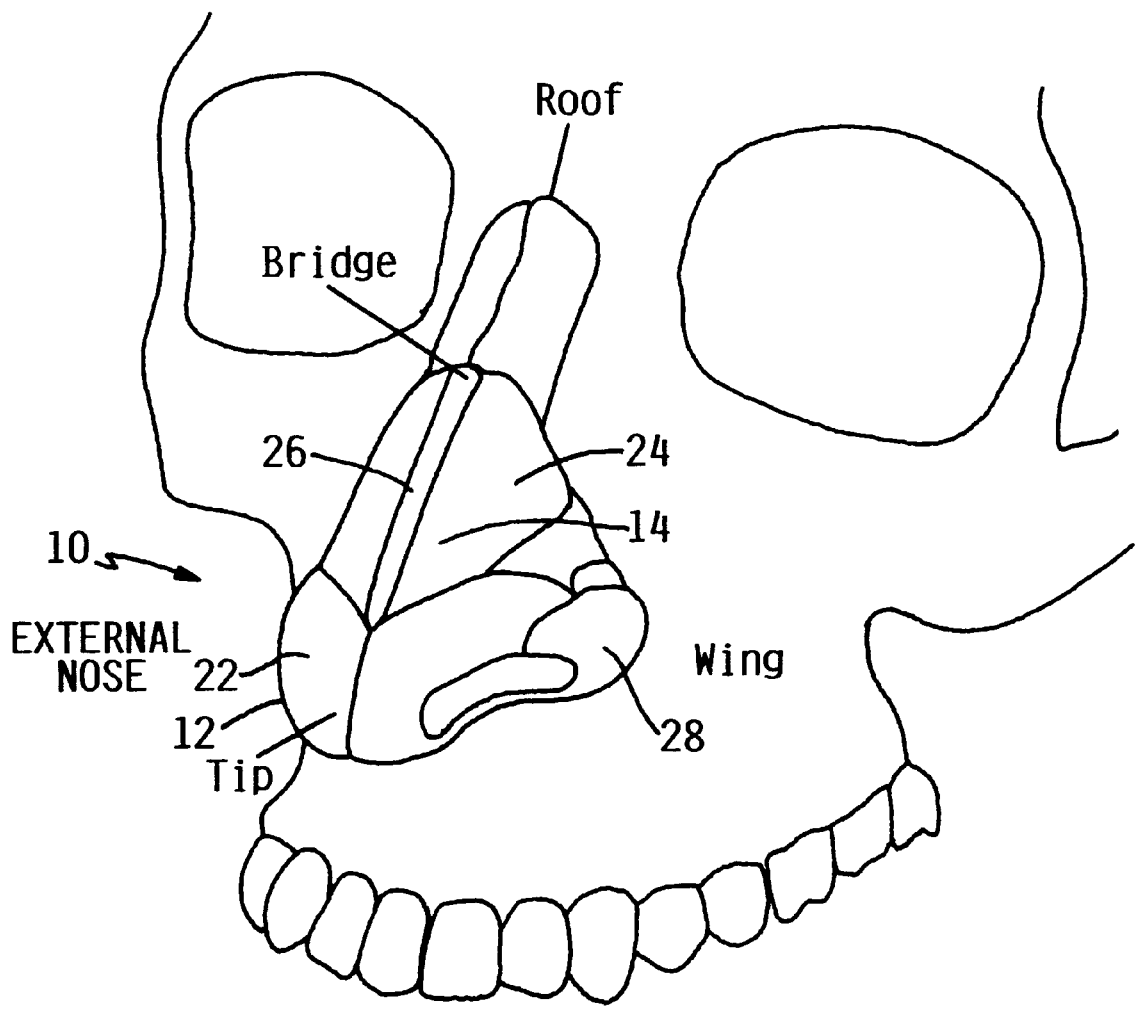
FIG. 13 is a diagrammatic illustration of the external nose.
Figure 14:
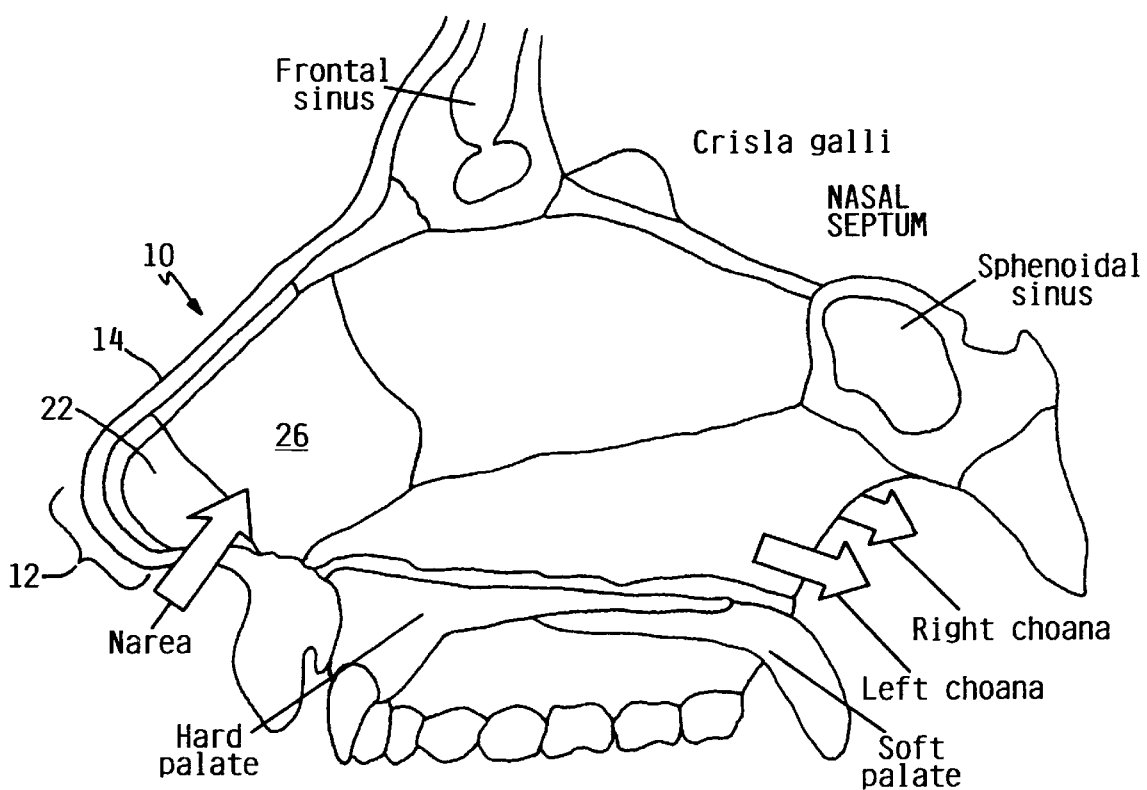
FIG. 14 is a diagrammatic illustration of the nasal septum
Figure 15:
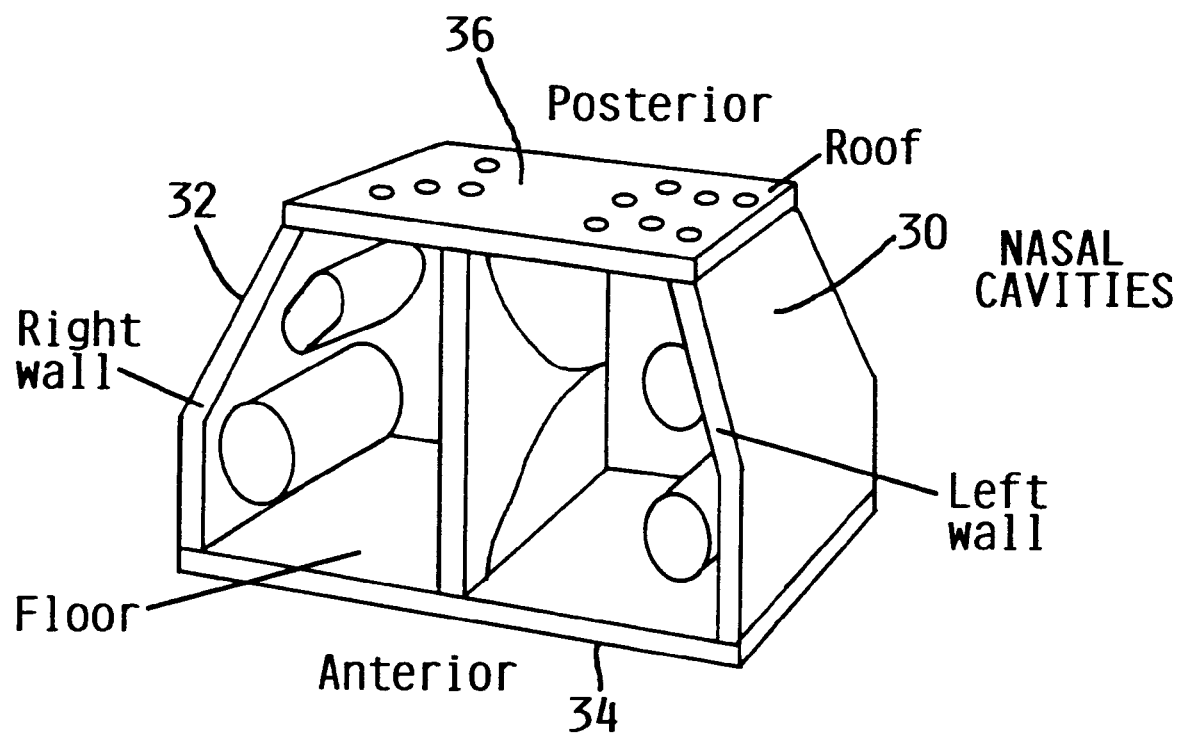
FIG. 15 is a diagrammatic illustration of the nasal cavities.

Nose structure is shown in FIGS. 13, 14, and 15. Reference numeral 10 generally indicates a nose. Nose 10 includes a tip 12 and a bridge 14. It is preferred that one end portion of the present nose foreshortener, described below, is placed on or beyond the tip 10 of the nose and the other end portion of the nose foreshortener is placed above the tip such as on the bridge 14 of the nose. Or, if desired, one end portion may be placed on skin tissue immediately on the alar cartilage 22 and the other end portion may be placed on skin tissue immediately on the lateral nasal cartilage 24 or immediately on the nasal septum cartilage 26. The bridge 14 of the nose 10 may generally be defined for the purposes of the present invention as running the length of the lateral nasal cartilage 24. The nose 10 further includes fibro-fatty tissue 28. The nose foreshortener at least shortens or compresses the alar cartilage 12. The nose foreshortener may further compress the lateral nasal cartilage 24, the nasal septum cartilage 26, and the fibro-fatty tissue 28. When one or more of such cartilage is compressed, the nasal passages dilate. More specifically, one or more of the left wall 30, right wall 32, floor 34, or roof 36 of the nasal cavities are pulled outwardly by such compressed or shortened cartilage. Further, during snoring, the nose foreshortener minimizes vibration of the fibro-fatty tissue 28 and the lateral nasal cartilage 24. As to nose structure and such cartilage, the following reference, particularly page 92, is hereby incorporated by reference in its entirety: KAPIT and ELSON, *The Anatomy Coloring Book*, 1993, Second Edition, HarperCollins College Publishers, New York.

In the Figures, a nose foreshortener, such as referred to above, is indicated in general by the reference numbers 40, 50, 60, 70, and 80.

In the Figures, one end portion of such respective nose foreshorteners, is indicated by the respective reference numbers 42, 52, 62, 72, and 82. This is the nose tip end portion or the portion to be applied on or beyond the tip of the nose. This nose tip end portion is preferably applied on or beyond the tip of the nose to get around the curvature or circumference of the tip of the nose such that when this tip end portion is being pulled by the anchoring end portion (described immediately below), this tip end portion compresses the cartilage 22 and other cartilage instead of merely pulling skin up if applied too far up the nose such as too far up the bridge of the nose.

In the Figures, the other end portion, the anchoring end portion, of such respective nose foreshorteners, is indicated by the respective reference numbers 44, 54, 64, 74, and 84. This is the anchoring end portion to be applied to the bridge of the nose.

Each of the nose foreshorteners have an outer visible face and an inner face. At least sections of the inner face on the end portions have adhesive A thereon.

Each of the nose foreshorteners further has a liner L or, more specifically, two liner portions covering the adhesive. Each of the liners or liner portions is removable from its adhesive.

FIGS. 2, 3, 4, and 6 show transversely oriented spring nasal dilators 90, 92, and 94. As to such spring nasal dilators, the Johnson U.S. Pat. No. 5,533,499 entitled Nasal Dilator and the Doubek et al. U.S. Pat. No. 5,533,503 are hereby incorporated by reference in their entireties.

Spring nasal dilators 90, 92 and 94 each have a plastic flat spring 90a, 92a, and 94a embedded therein. Flat springs 92 and 94 form substantially the shape of an inverted V when in their flat from each of the transverse nasal dilators have an inner adhesive face and a removable liner on such inner adhesive face.

Tip end portions 42 and 52 are integral with their transversely oriented spring nasal dilators. Such is preferred. However, if desired, nose foreshorteners or strips 60, 70 and 80 may be used in combination with a transversely oriented spring nasal dilator, such as one of the dilators shown and described in the above referenced U.S. Pat. Nos. 5,533,499 and 5,533,503. In such a case, it is preferred that the transversely oriented spring nasal dilator is first placed on the nose and that subsequently the nose foreshortener strip is placed on the nose so as to use the exterior face of the transversely oriented nasal dilator as an anchor. Such an anchor is nonoily, unlike the skin of the nose.

As to the material for the nose foreshorteners 40, 50, 60, 70, and 80, the Johnson U.S. Pat. No. 5,533,499 entitled Nasal Dilator and the Doubek et al. U.S. Pat. No. 5,533,503 are hereby incorporated by reference in their entireties. As to the adhesive for such nose foreshorteners, the Johnson U.S. Pat. No. 5,533,499 entitled Nasal Dilator and the Doubek et al. U.S. Pat. No. 5,533,503 are hereby incorporated by reference in their entireties. As to the liners for such nose foreshorteners, the Johnson U.S. Pat. No. 5,533,499 entitled Nasal Dilator and the Doubek et al. U.S. Pat. No. 5,533,503 are hereby incorporated by reference in their entireties.

The material for such nose foreshorteners may be clear or translucent or opaque.

The adhesive for such nose foreshorteners is preferably nonallergenic.

It is preferred that the liner include two liner portions, such as two liner portions 100 and 102 separated by a score 104, shown in FIG. 5. Liner portion 102 defines the tip end portion 42 and covers adhesive on the inner face of such tip end portion 42. Liner portion 100 may cover adhesive along its entire length, but more preferably covers adhesive only at an upper portion such as a portion traversed by the transversely oriented spring nasal dilator 90. Further score lines are indicated by reference numerals 106, 108, 110, and 112. Liner portions are defined by such score lines, and the shapes of the liner portions are defined by the shapes of the nose foreshortener strips above and below these score lines.

It should be noted that the nose foreshorteners 40, 50, 60, 70, and 80 each includes a respective neck 114, 116, 118, 120, and 122. Each of the necks runs between the anchoring end portion and the tip end portion and includes a width less than the width of either of such end portions. It is preferred that each of the necks includes a less amount of adhesive than the end portions or a less sticky adhesive. It is more preferred that each of the necks includes no adhesive.

The present invention includes a method of applying the nose foreshortener. Such method of the present invention for foreshortening the nose uses a first strip including a pair of opposite end portions, with each of the opposite end portions having an inner face and an adhesive on at least a section of each of the inner faces of the opposite end portions. The first strip further includes a removable liner over the adhesive. The method includes the steps of a) removing the liner from the adhesive; b) pushing up the tip of a nose in a direction generally toward the eyes; c) applying one of the end portions to a position on or beyond the tip of the nose; and d) applying the other of the end portions to the bridge of the nose such that the tip of the nose is held up whereby the nose is foreshortened.

The liner may include two liner portions separated by a score, with one of the liner portions covering adhesive on one of the end portions and the other liner portion covering adhesive on the other end portion. In such a case, the step of removing the liner from the adhesive includes the steps of first removing the liner portion from the end portion to be applied to the position on or beyond the tip of the nose and then removing the other liner portion, with such latter step of then removing the other liner portion occurring after the end portion to be applied on or beyond the tip of the nose has been applied to the position on or beyond the tip of the nose.

Figure 1:
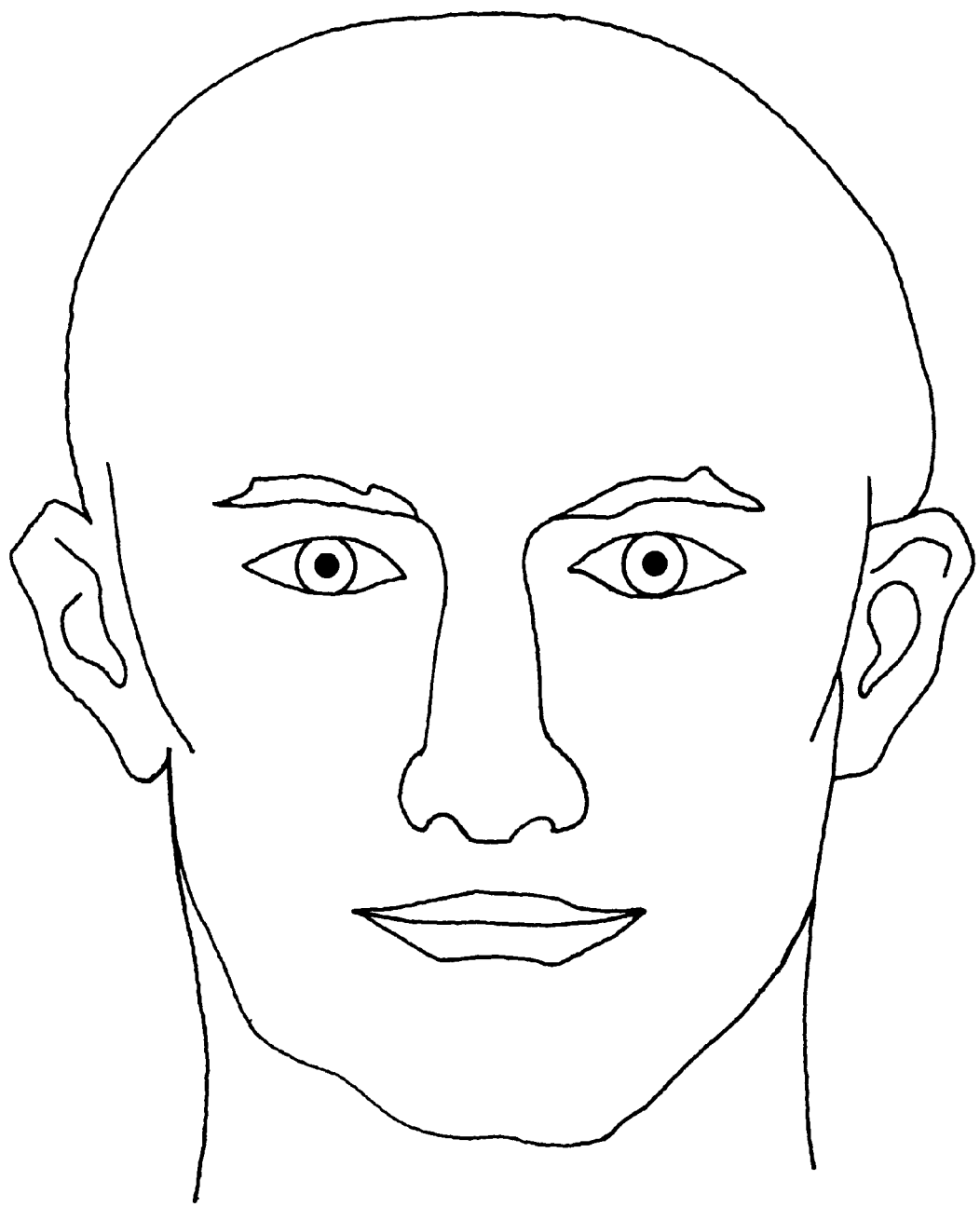
FIG. 1 shows a frontal view of a face before the present nose foreshortener is applied to the face.
Figure 2:
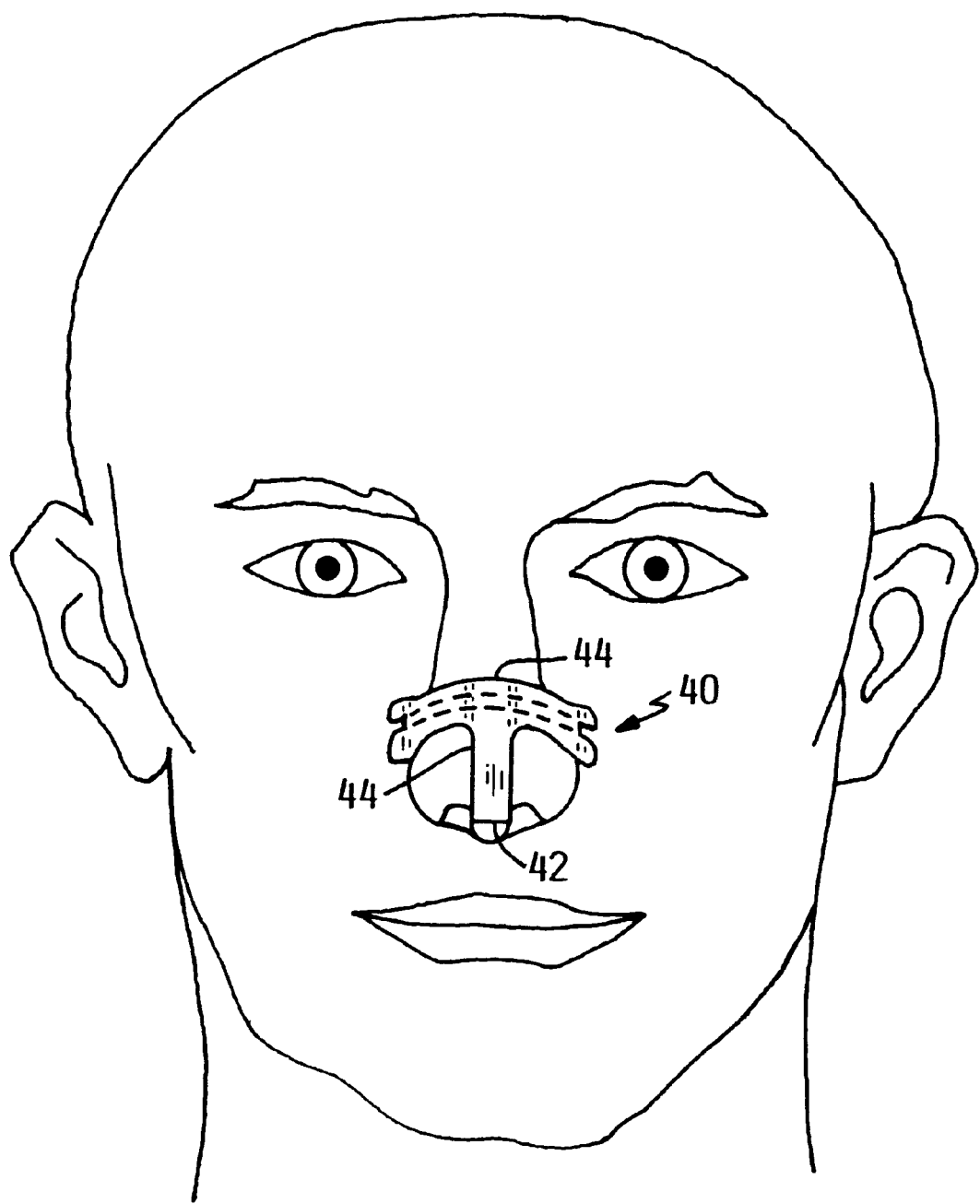
FIG. 2 shows a frontal view of the face of FIG. 1 with the present nose foreshortener applied thereto.
Figure 3:
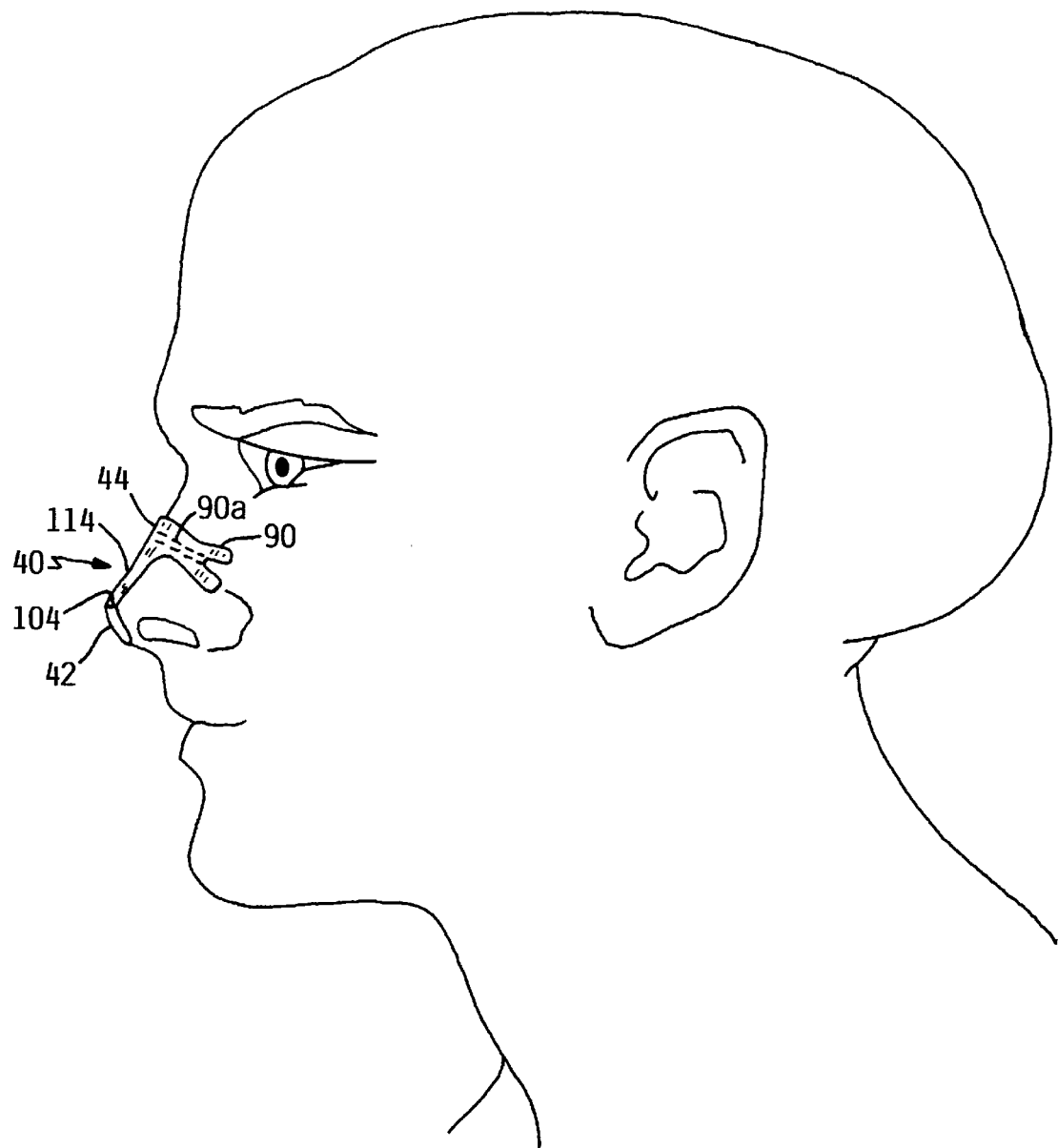
FIG. 3 shows a profile of the face of FIG. 3.
Figure 10:
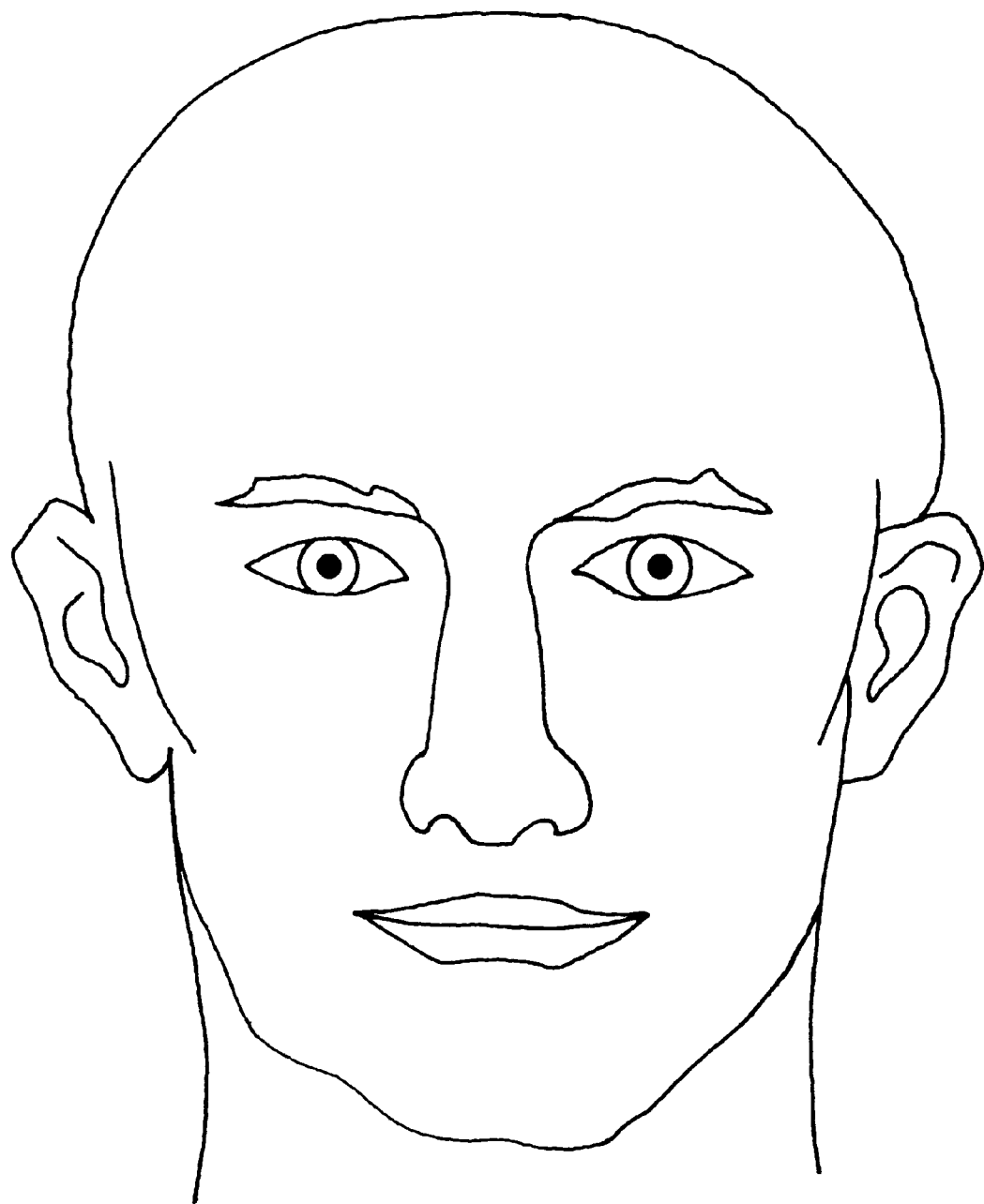
FIG. 10 shows a frontal view of a face before the nose foreshortener of FIG. 7 is applied to the face.
Figure 11:
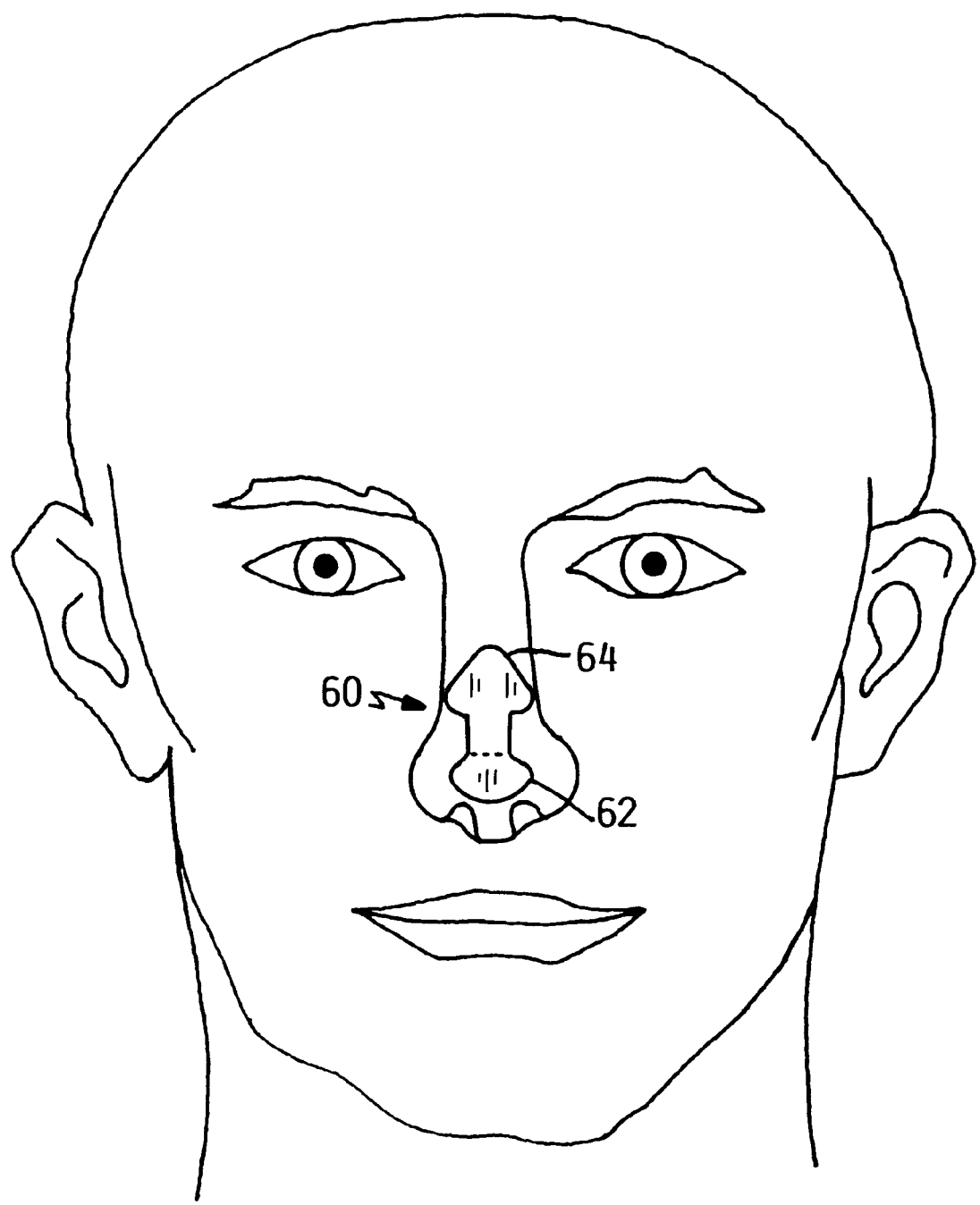
FIG. 11 shows a frontal view of the face of FIG. 10 with the nose foreshortener of FIG. 7 applied thereto.
Figure 12:
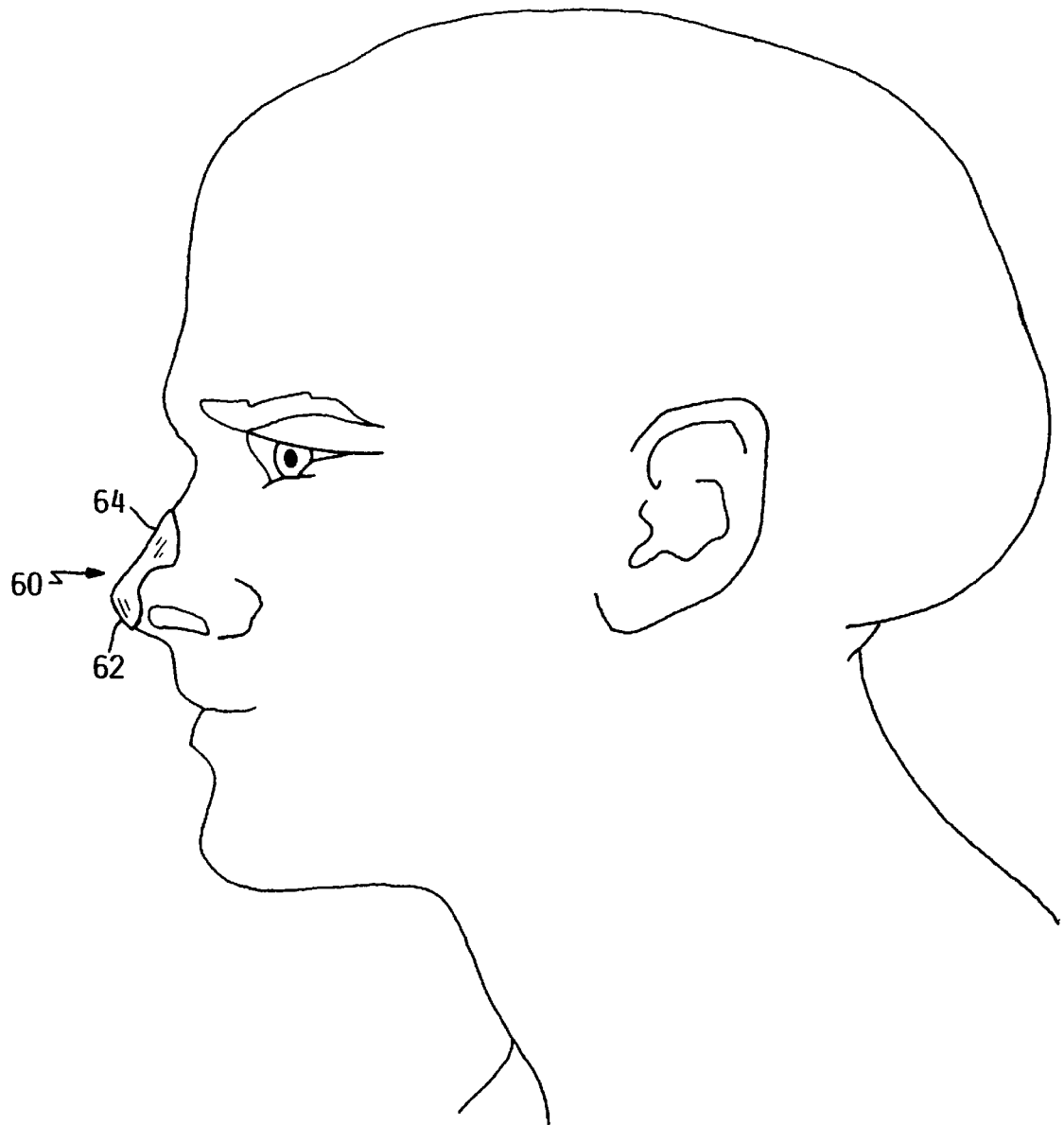
FIG. 12 shows a profile of the face of FIG. 11 having the nose foreshortener of FIG. 7 applied thereto.

FIGS. 1 and 10 shows a facial structure prior to the present nose foreshortener being applied. FIGS. 2 and 3 and FIGS. 11 and 12 show the same facial structure after the nose foreshortener has been applied. After application, in FIGS. 2 and 3 and in FIGS. 11 and 12, the nostrils of the nose have been opened upwardly and further have been dilated.

It should be noted that the present nose foreshortener is a nasal passage enlarger and straightener device. Its purpose is to assist greater volume of air in an intake of breath with less effort and reduce natural air intake blockages.

Noses have different sizes, shapes and lengths. However, most if not all noses have opening that increase in diameter when foreshortened.

When you place a finger under your nose and push up on the tip of the nose, you will find an increase in nasal passage air capacity. The improvement is to add an adhesive backed or woven or nonwoven base strip under the nasal dilators such as in the Johnson U.S. Pat. No. 5,533,499 entitled Nasal Dilator and the Doubek et al. U.S. Pat. No. 5,533,503. When applying the extension, i.e., the nose foreshortener, clean the skin between the nostrils under the nose as well as the area above the tip of the nose where the standard transversely oriented spring nasal dilator is applied. Remove the liner or liner portions from the nose foreshortener and apply the narrow strip under the nose between the nostrils. Then grasp the nose foreshortener in the top middle portion, such as at the neck, and pull up snugly to where the tip of the nose is comfortably compressed. This action will lift the tip of the nose and foreshorten the nose and compress the cartilage referred to above. Then remove the liner portion from the anchoring end portion of the nose foreshortener and apply such portion to the bridge of the nose. Then apply the integral transversely oriented nasal dilator, i.e. the second strip or the transverse strip to the right and left sides of the nose.

The present nose foreshorteners when used by itself or in conjunction with the transversely oriented spring nasal dilator permits more air to flow through the nose to the lungs thereby minimizing snoring, maximizing the volume of air flowing to the lungs, maximizing the rate of air inhaled and exhaled, and minimizing the effort needed to inhale and exhale.

It should be noted that nose foreshortener of FIG. 9 shows end portions 82 and 84 which are substantially immediately adjacent to one another. Here, the neck 122 may traverse the transition from the alar cartilage 22 to the lateral nasal cartilage 24.

It should be noted that the nose foreshortener shown in FIG. 7 has end portions 62 and 64 generally reflecting the shape of diamonds or arrowheads with three rounded points 130, 132, and 134 on one end and three rounded points 140, 142, and 144 on the other end.

If desired, transversely oriented end portion 84 may have a flat plastic spring embedded therein to function like the plastic springs in FIGS. 4 and 6.

It is preferred to space the tip end portion of the nose foreshortener from the upper lip. It is even more preferred to terminate the tip end portion at a position above the area directly between the nostrils as such an area includes tender skin. However, given such, it is preferred that the tip end portion be on or beyond the end of the nose so as to utilize as the rounding of the nose for leverage for the pulling and compressing action desired by the nose foreshortener.

Thus since the invention disclosed herein may be embodied in other specific forms without departing from the spirit or general characteristics thereof some of which forms have been indicated, the embodiments described herein are to be considered in all respects illustrative and not restrictive. The scope of the invention is to be indicated by the appended claims, rather than by the foregoing description, and all changes which come within the meaning and range of equivalents of the claims are intended to be embraced therein.

I claim:

1. A nose foreshortener, comprising:
    a) a first strip comprising a pair of opposite end portions, with each of the opposite end portions having an inner face; and
    b) an adhesive on at least a section of each of the inner faces of the opposite end portions wherein one of the end portions adheres on or beyond the tip of the nose and wherein the other of the end portions adheres to the bridge of the nose, whereby the nose is foreshortened.

2. The nose foreshortener according to claim 1, and further comprising a second strip comprising an inner face having an adhesive, with the second strip being placed via such adhesive on the nose across the bridge of the nose, with the second strip running transversely to the first strip.

3. The nose foreshortener according to claim 2 wherein the first and second strips are integral with each other.

4. The nose foreshortener according to claim 1 wherein the strip includes a neck integral with and disposed between the two end portions, and wherein the neck includes an inner face, with a section of the inner face being void of adhesive.

5. The nose foreshortener according to claim 1 and further comprising a liner on the adhesive of the inner face, with the liner being removable to expose the adhesive.

6. The nose foreshortener according to claim 5 wherein the liner comprises two liner portions separated by a score, with one of the liner portions having a shape substantially the same as one of the end portions such that the adhesive of the end portions may be exposed at different times.

7. The nose foreshortener according to claim 1 wherein the strip includes a predetermined length such that the end portion adhered on or beyond the tip of the nose terminates immediately beyond the tip of the nose.

8. The nose foreshortener according to claim 1 wherein the strip includes a predetermined length such that the end portion adhered on or beyond the tip of the nose terminates at a position between the nostrils of the nose.

9. The nose foreshortener according to claim 2 wherein the second strip forms an inverted V-shape.

10. The nose foreshortener according to claim 2 and further comprising another second strip running transversely to the first strip, with said another second strip crossing the first strip between the end portions.

11. The nose foreshortener according to claim 1 wherein one of the end portions comprises a tip and edge portions tapering toward each other to form said tip, and wherein the tip of said end portion is rounded.

12. The nose foreshortener according to claim 1 wherein each of the end portions forms generally a diamond shape comprising three rounded diamond tips.

13. The nose foreshortener according to claim 1 wherein one of the end portions comprises a transverse strip portion extending transversely across the bridge of the nose when adhered to the bridge of the nose and with the transverse strip including opposite inner face sections having adhesive for engaging nostril skin portions of the nose, and wherein the other end portion terminates immediately beyond the end of the nose when adhered to the end of the nose.

14. A method for foreshortening the nose with a first strip comprising a pair of opposite end portions, with each of the opposite end portions having an inner face and an adhesive on at least a section of each of the inner faces of the opposite end portions, with the first strip further comprising a removable liner over the adhesive, comprising the steps of:

a) removing the liner from the adhesive;

b) pushing up the tip of a nose in a direction generally toward the eyes;

c) adhering one of the end portions to a position on or beyond the tip of the nose;

d) adhering the other of the end portions to the bridge of the nose such that the tip of the nose is held up whereby the nose is foreshortened.

15. The method of claim 14 wherein the liner comprises two liner portions separated by a score, with one of the liner portions covering adhesive on one of the end portions and the other liner portion covering adhesive on the other end portion, and wherein the step of removing the liner from the adhesive comprises the steps of first removing the liner portion from the end portion to be adhered to the position on or beyond the tip of the nose and then removing the other liner portion, with such latter step of then removing the other liner portion occurring after the end portion to be adhered on or beyond the tip of the nose has been adhered to the position on or beyond the tip of the nose.

\* \* \* \* \*